United States Patent

Saito et al.

[11] Patent Number: 4,491,667
[45] Date of Patent: Jan. 1, 1985

[54] HEXAHYDROPHTHALIDES

[75] Inventors: Takayuki Saito; Toru Kikuchi; Masakatsu Obara; Akihiro Kobayashi, all of Hitachi, Japan

[73] Assignee: Hitachi Chemical Company, Ltd., Tokyo, Japan

[21] Appl. No.: 388,244

[22] Filed: Jun. 14, 1982

[30] Foreign Application Priority Data

Jun. 17, 1981 [JP] Japan .................................. 56-94164
Apr. 27, 1982 [JP] Japan .................................. 57-70921

[51] Int. Cl.³ ........................................... C07D 307/77
[52] U.S. Cl. .................................................. 549/302
[58] Field of Search ........................................ 549/302

[56] References Cited

U.S. PATENT DOCUMENTS 2,007,813  7/1935  Scheuing et al. .................... 549/302
2,731,475  1/1956  Hillyer et al. ........................ 549/302

Primary Examiner—Jane T. Fan
Attorney, Agent, or Firm—Antonelli, Terry & Wands

[57] ABSTRACT

A lactone of the formula:

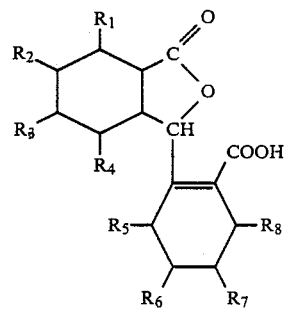

wherein $R_1$ through $R_8$ are independently hydrogen or $C_{1-5}$ alkyl, obtained by decarboxylation condensation reaction of a saturated alicyclic 1,2-dicarboxylic acid anhydride, is a good curing agent for thermosetting resins.

1 Claim, 6 Drawing Figures

FIG. 1

ELUTION TIME (MINS)

HEXAHYDROPHTHALIDES

This invention relates to a lactone and a process for producing said lactone by carrying out a decarboxylation condensation reaction of a saturated alicyclic 1,2-dicarboxylic acid anhydride.

As a lactone derived from a decarboxylic acid anhydride by a decarboxylation condensation reaction, there has so far been reported only spirodilactone represented by the formula:

(I)

which is obtained by conducting a decarboxylation condensation reaction of succinic anhydride at high temperatures (J. Volhard, Ann., 253, 206 (1890)).

This spirolactone structurally has two lactone rings in the molecule. When reacted with water, this compound is rearranged, as shown by the following equation, to be converted into a dibasic acid (4-ketopimelic acid) of the formula (II) having a number of functional groups of 2 which is equal to those of ordinary dicarboxylic acid anhydrides.

(II)

In general, as a lactone derivable from a dicarboxylic acid anhydride, there has been known no lactone except the aforesaid spirodilactone.

An object of this invention is to provide a lactone which, unlike such a lactone having two lactone rings in the molecule, is obtained by a decarboxylation condensation reaction, and to provide a process for production thereof.

This invention provides a lactone of the formula:

(III)

wherein $R_1$, $R_2$, $R_3$, $R_4$, $R_5$, $R_6$, $R_7$ and $R_8$ are independently hydrogen or an alkyl group having 1 to 5 carbon atoms, produced by decarboxylation condensation of a saturated alicyclic 1,2-dicarboxylic acid anhydride.

This invention also provides a process for producing a lactone of the formula (III) by conducting a decarboxylation condensation reaction of a saturated alicyclic 1,2-dicarboxylic acid anhydride in the presence of a basic catalyst with heating.

In the attached drawings.

The lactone represented by the formula (III) is characterized by having a lactone ring fused together with a cyclohexane ring; having a cyclohexene ring with an unsaturated double bond attached to said lactone ring; and having a carboxyl group joined to said cyclohexene ring. When hydrolyzed, said lactone is converted into an oxydicarboxylic acid represented by the formula:

(IV)

wherein $R_1$, $R_2$, $R_3$, $R_4$, $R_5$, $R_6$, $R_7$ and $R_8$ are as defined above, and therefore it is greatly different from the aforesaid spirodilactone.

The lactones represented by the formula (III) can effectively be used, for example, as curing agents for thermosetting resins such as epoxy resins.

Among the lactones represented by the formula (III), those represented by the formula:

(V)

wherein $R_9$ and $R_{10}$ are independently hydrogen or an alkyl group having 1 to 5 carbon atoms, $R_9$ may be attached to any place among 3- to 6-positions, and $R_{10}$ may be attached to any place among 9- to 12-positions, are particularly preferred as curing agents for epoxy resins. Among the lactones of the formula (V), those in which $R_9$ and/or $R_{10}$ are independently an alkyl group having 1 to 5 carbon atoms are preferable, and those in which $R_9$ and/or $R_{10}$ are independently a methyl group are more preferable. The methyl substituted lactones are more preferable because these lactones are readily dissolved in epoxy resin as well as in a number of different organic solvents.

The lactone of this invention represented by the formula (III) can be obtained, for example, by conducting a reaction (a decarboxylation condensation reaction) of a saturated alicyclic 1,2-dicarboxylic acid anhydride of the following formula:

(VI)

wherein $R_{11}$, $R_{12}$, $R_{13}$ and $R_{14}$ are independently hydrogen or an alkyl group having 1 to 5 carbon atoms, in the presence of a basic catalyst with heating.

Examples of the saturated alicyclic 1,2-dicarboxylic acid anhydride represented by the above formula (VI) are hexahydrophthalic anhydride, 3-methylhexahydrophthalic anhydride, 4-methylhexahydrophthalic anhydride, and the like. These may be used alone or as a mixture thereof. Dicarboxylic acids formed by ring opening of these acid anhydrides may also be used as starting material. However, in this case, the reaction temperature should be elevated because said dicarboxylic acids are converted into their acid anhydrides and then undergo the decarboxylation condensation reaction.

In this invention, as the saturated alicyclic 1,2-dicarboxylic acid, monocyclic saturated alicyclic 1,2-dicarboxylic acids such as those represented by the above formula (VI) are preferred. From them, the lactone, i.e. the decarboxylation condensation product of this invention is easy to obtain. As the saturated alicyclic 1,2-dicarboxylic acid, there may also be used besides them polycyclic 1,2-dicarboxylic acid anhydrides formed by fusion of monocyclic alicyclic structures and containing no unsaturated bond in the ring structure to which an acid anhydride group is bonded.

As the basic catalyst, there may be used, for example, amine compounds such as 1,8-diazabicyclo[5,4,0]undecene-7 (hereinafter abbreviated as "DBU"), 2-ethyl-4-methylimidazole, dibutylaniline, benzyldimethylamine and the like; phosphorus compounds such as triphenylphosphine, hexamethylphosphatriamide and the like; alkali metal hydroxides such as KOH, NaOH and the like; alkoxides of alkali metals such as $NaOCH_3$ and the like; hydroxides of alkaline earth metals such as $Mg(OH)_2$, $Ca(OH)_2$, $Ba(OH)_2$ and the like; and oxides of alkaline earth metals such as MgO, CaO, BaO and the like. As particularly preferable catalysts, there may be exemplified strongly basic catalysts such as DBU, 2-ethyl-4-methylimidazole, KOH, NaOH and the like.

The amount of these catalysts to be used is preferably 0.1% by weight or more based on the aforesaid saturated alicyclic 1,2-dicarboxylic anhydride. When it is less than 0.1% by weight, the reaction becomes slow. The catalyst amount is not particularly limited when it is 0.1% by weight or more but in usual, 5% by weight or less is sufficient.

The reaction temperature is preferably 160° to 250° C. When it is lower than 160° C., the reaction becomes slow. On the other hand, when it is too high, the product is seriously colored and by-products having high molecular weights tend to be formed: therefore it is preferable not exceeding 250° C.

The reaction may be effected in an organic solvent.

Since carbon dioxide is produced during the above-mentioned reaction, the progress of the decarboxylation condensation reaction can be known. The basic catalyst may remain in the mixture obtained by the decarboxylation condensation reaction. The catalyst can be removed by a usual procedure, for example, a method comprising neutralizing said mixture by adding activated clay (acid clay) with heating or after the addition of a solvent, and then filtering the resulting mixture, or a method comprising dissolving the reaction product in a solvent immiscible with water and then washing it with water. Particularly when the mixture having undergone the reaction contains a saturated alicyclic 1,2-dicarboxylic acid, the method comprising washing with water is preferred because said dicarboxylic acid can be removed simultaneously with the removal of the catalyst.

When unreacted saturated alicyclic 1,2-dicarboxylic acid anhydride remains, it can be removed by heating the mixture having undergone the reaction together with additional water in a solvent such as tetrahydrofuran, dioxane or the like at 60° to 70° C. to subject said acid anhydride to ring-opening and convert it into the dicarboxylic acid, distilling off the solvent, and then washing the residue with water. However, the lactone of the formula (III) of this invention may be used without particular purification.

The novel lactone of this invention does not undergo the ring-opening of the lactone ring at 60° to 70° C.

The lactone of the formula (III), i.e., the decarboxylation condensation product produced according to this invention has one lactone ring, one carboxyl group and at least one double bond (newly introduced into the carbon ring), which are easily identified from mass spectrum, NMR spectrum, IR spectrum and the $KMnO_4$ qualitative reaction.

This invention is further explained below in more detail referring to Examples.

EXAMPLE 1

Into a 200 ml four-necked flask equipped with a stirrer, a thermometer and a reflux condenser was charged 100 g of hexahydrophthalic anhydride and the temperature of the contents of the flask was raised with heating under stirring. When the temperature of the contents reached 200° C., 1.0 g of DBU was added dropwise. On dropwise addition of DBU, vigorous evolution of carbon dioxide gas was observed. The flask was maintained at 200° C. for 3 hours while the contents were further stirred. Thereafter, the contents were cooled to 100° C. and then dispersed into a xylene solvent, after which the resulting dispersion was filtered to obtain white powder. The white powder was washed with water and dried to obtain 81.5 g of a decarboxylation condensation product (A).

Figure 1:
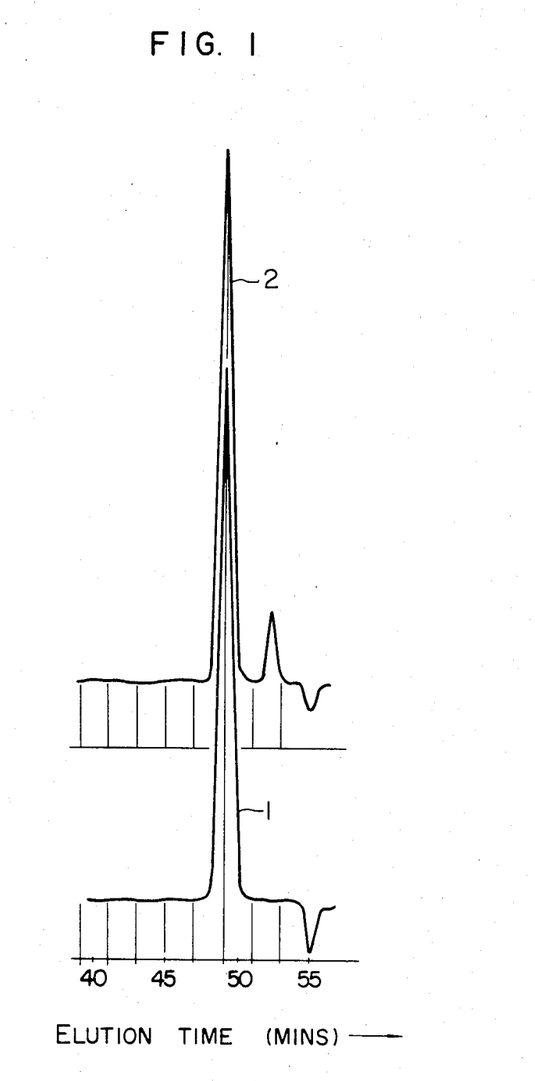
FIG. 1 shows chromatograms obtained by analyzing the decarboxylation condensation product (A) and the reaction solution in Example 1 by high-speed liquid chromatography (hereinafter abbreviated as "HLC")

The decarboxylation condensation product (A) was identified as a compound represented by the formula:

(VII)

from the following analyses. First, the aforesaid decarboxylation condensation product (A) was analyzed by high-speed liquid chromatography (hereinafter abbreviated as "HLC"). In the above, a part of the reaction solution subjected to 1 hour's reaction after the dropwise addition of DBU was sampled and then analyzed by HLC. The analysis conditions were as follows:

Column: Packing GELKO A-120 [a trade name, manufactured by Hitachi Chemical Co., Ltd., porous styrene-divinylbenzene copolymer particles, exclusive limit $5 \times 10^3$] Two columns having an inside diameter of 8 mm and a length of 50 cm were connected in series.
Solvent: Tetrahydrofuran
Flow rate of solvent: 0.6 ml/min
Column pressure: 30 kg/cm$^2$
Detector: Differential refractometer The results of the above-mentioned analysis are shown in FIG. 1. In FIG. 1, the chromatogram 1 shows an analysis result for the decarboxylation condensation product (A) and the chromatogram 2 that for the reaction solution. Although these chromatograms were measured separately, these are shown in FIG. 1 one over the other on the same elution time scale. In the chromatograms 1 and 2, the negative absorptions are due to impurities in tetrahydrofuran. In the chromatogram 2, the weak absorption is due to hexahydrophthalic anhydride, and from the fact that this absorption is not observed in the chromatogram 1, it can be seen that the decarboxylation condensation product (A) does not contain the starting hexahydrophthalic anhydride. It can also be seen that the decarboxylation condensation product (A) has a higher molecular weight than does hexahydrophthalic anhydride.

Next, elementary analysis results for the obtained decarboxylation condensation product (A) are shown in Table 1.

TABLE 1

|  | Analytical value | Theoretical value |
|---|---|---|
| Carbon (% by weight) | 67.54 | 68.16 |
| Hydrogen (% by weight) | 7.68 | 7.63 |
| Oxygen (% by weight) (balance) | 24.78 | 24.21 |

From these measurement results, the empirical formula was determined to be $C_{15.0}H_{20.3}O_{4.1}$. When these values are compared with the values in $C_{16}H_{20}O_6$, i.e., twice the values in the rational formula $(C_8H_{10}O_3)$ of hexahydrophthalic anhydride, it can be seen that said empirical formula clearly lacks 1 mole of $CO_2$.

That is to say, it can be seen that 2 moles of the hexahydrophthalic anhydride was converted into the decarboxylation condensation product (A) with release of 1 mole of carbon dioxide gas by the decarboxylation condensation reaction.

Figure 2:
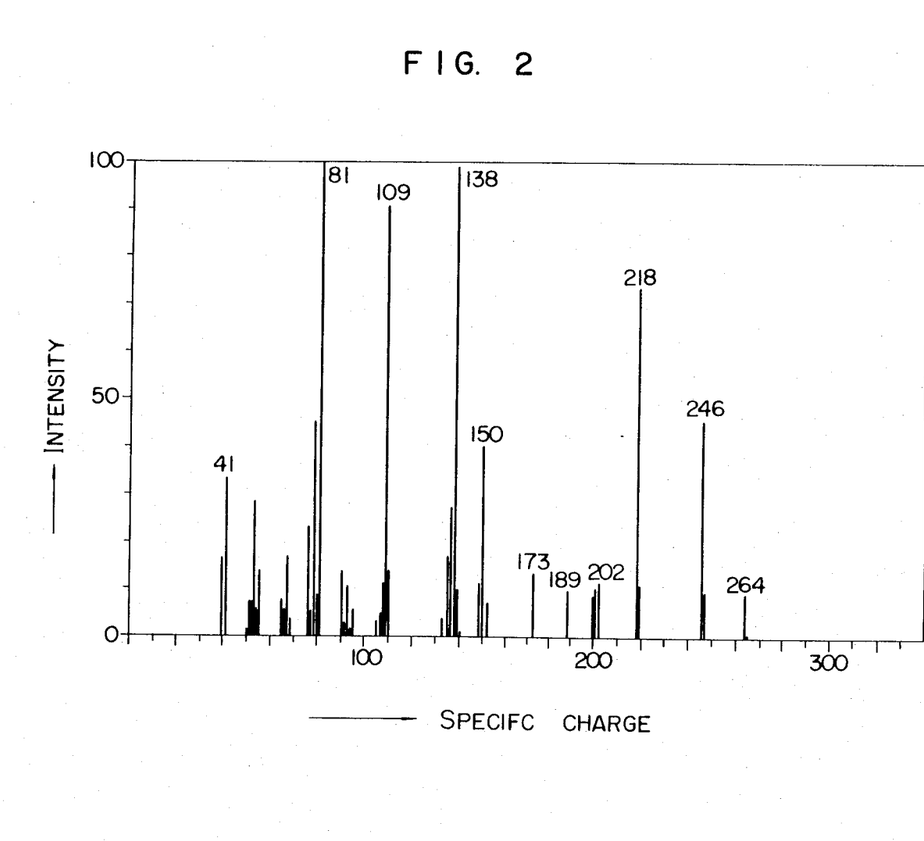
FIG. 2 shows a mass spectrum of the decarboxylation condensation product (A)

In order to confirm the HLC and elementary analysis results, the molecular weight of the decarboxylation condensation product (A) was measured by using a mass spectrographic apparatus. The obtained spectrum is shown in FIG. 2. A parent peak is at a specific charge of 264, and hence the molecular weight of the decarboxylation condensation product (A) is 264. That is to say, it can be seen that decarboxylation condensation product (A) is the decarboxylation dimerization product of hexahydrophthalic anhydride and is a compound with a molecular weight of 264 having the rational formula $C_{15}H_{20}O_4$.

Figure 3:
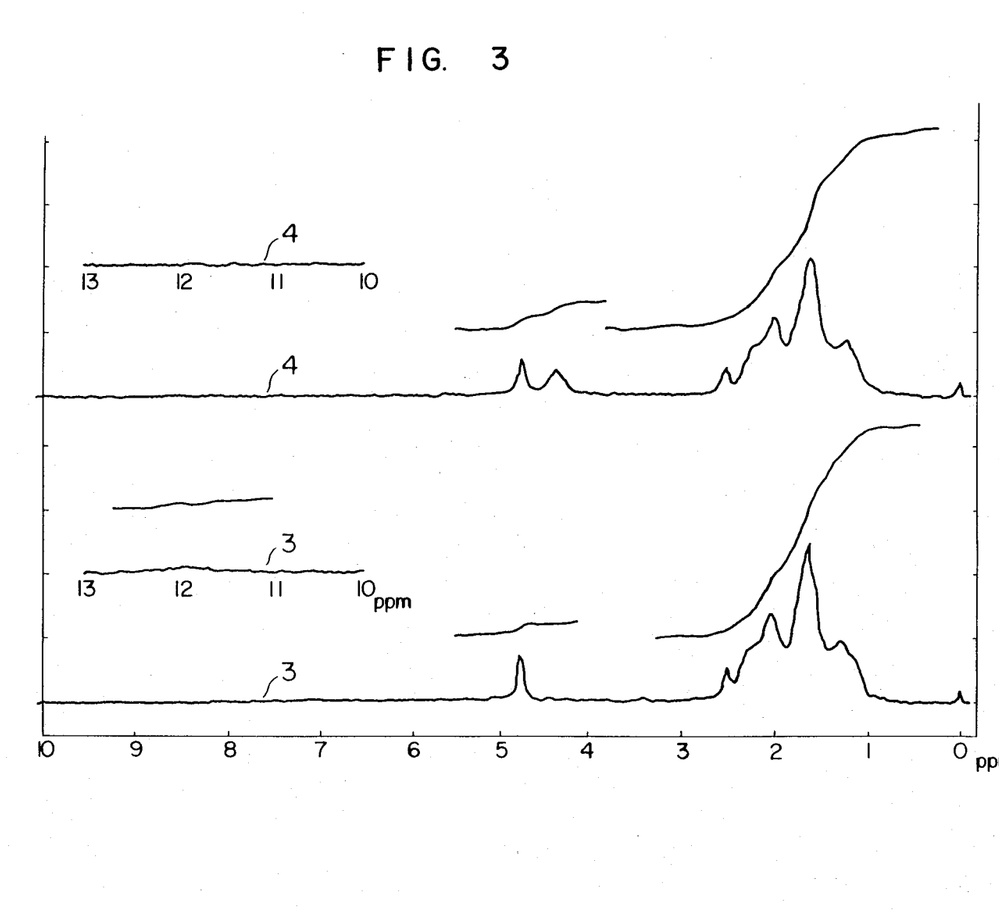
FIG. 3 shows nuclear magnetic resonance spectra (hereinafter abbreviated as "NMR spectra") of the decarboxylation condensation product (A)

Next, nuclear magnetic resonance (hereinafter abbreviated as "NMR") analysis results for the decarboxylation condensation product (A) are shown in FIG. 3. In FIG. 3, the spectrum 3 is the result of measurement in $d_6$-DMSO (demethylsulfoxide) solvent. A broad peak is observed in the place centering at a δ value of 12.0 ppm. There are observed:

a singlet at 12.0 ppm

COOH    area ratio 1 (1H)

a singlet at 4.77 ppm area ratio 1 (1H)

four overlapped peaks at 1.0 to 2.5 ppm

C—H    area ratio 18.2 (18H)

All the above-mentioned ppm values are δ values. The result of NMR analysis after the addition of heavy water to the aforesaid $d_6$-DMSO solvent is shown as a spectrum 4, in which the broad peak at a δ value of 12.0 ppm disappears and a new peak for water formed by DH exchange appears at 4.4 ppm. It can be seen from this fact that a carboxyl group is present in the decarboxylation condensation product (A). From the integrated intensity of the peak, the amount of protons of the carboxyl group is found to be 1/20th of the total amount of protons contained in the decarboxylation condensation product (A).

The peak at 4.77 ppm coincides with the absorption peak for protons of methine at the α-position in a carboxylic acid ester observed with γ-valerolactone, sec-butyl acetate and the like, and the amount of protons obtained from the integrated intensity of the peak at 4.77 ppm is 1/20th of the total amount of protons contained in the decarboxylation condensation product (A). That is to say, it can be seen that the decarboxylation condensation product (A) has one intramolecular ester, i.e., one lactone ring.

In order to confirm the presence of a carboxyl group and its amount, the acid value was measured with potassium hydroxide. As a result, the acid value was found to be 214.5 (KOH mg/1 g of sample). This value is in good agreement with the theoretical acid value of 212.3 for a compound with a molecular weight of 264.3 having one carboxyl group.

By a qualitative test, the presence of an unsaturated bond was investigated with $KMnO_4$. An acetone solution of $KMnO_4$ was added dropwise to an acetone solution of the decarboxylation condensation product (A), and the resulting solution was allowed to stand at room temperature for 2 hours to find that the color of the solution changed from pink to brown. This fact indicates that the decarboxylation condensation product (A) has an unsaturated bond.

From the analysis results described above and the fact that the reaction is a decarboxylation reaction, the obtained decarboxylation condensation product (A) is found to have a structure represented by the above formula (VII).

The fact that the NMR spectra had no clearing peak at 4.5 to 6 ppm indicates that the unsaturated bond is a tetra-substituted carbon-carbon bond C=C (an unsaturated carbon-carbon double bond). From the fact that the mass spectrometry results indicate the presence of a strong fragment at a specific charge of 138, the structure of the decarboxylation condensation product is also found to be represented by the formula (VII).

Figure 4:
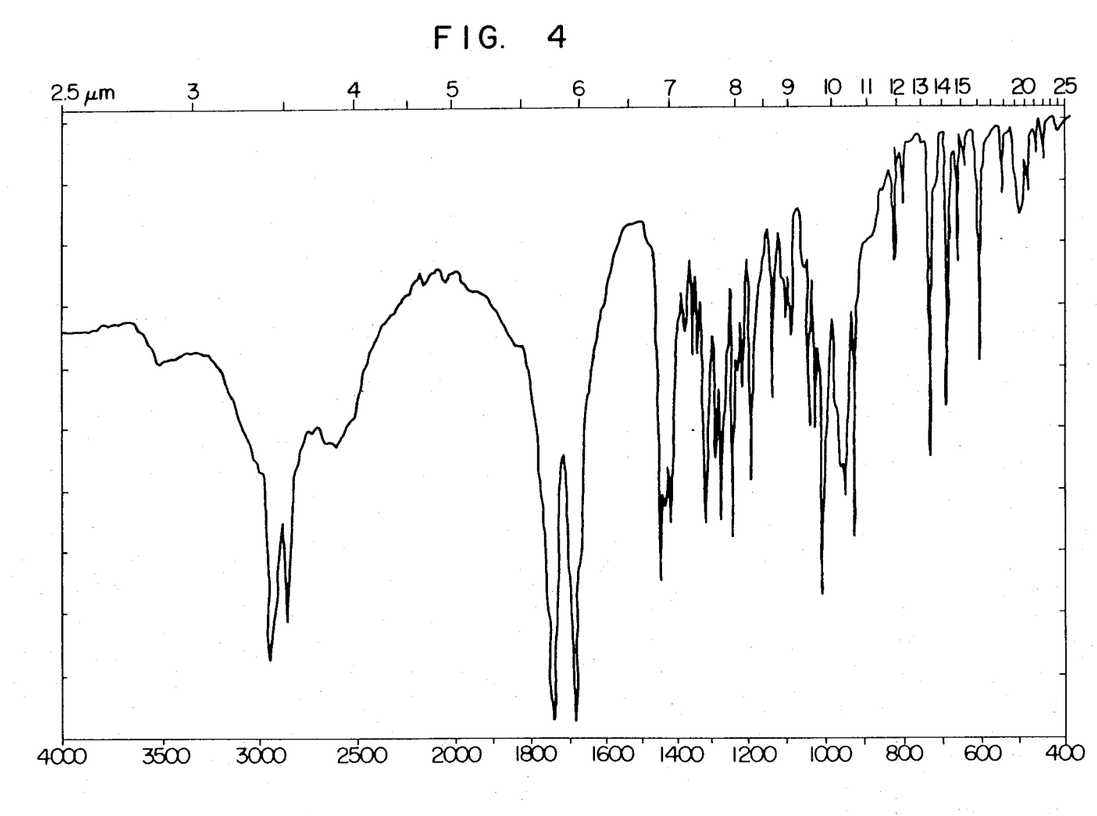
FIG. 4 shows an infrared absorption spectrum of the decarboxylation condensation product (A)

The infrared absorption spectrum (obtained by the KBr method) of the decarboxylation condensation product (A) is shown in FIG. 4. Strong absorptions due to the carbonyl group are observed at 1750 $cm^{-1}$ and 1690 $cm^{-1}$.

EXAMPLE 2

A reaction was effected in exactly the same manner as in Example 1, except that 4-methylhexahydrophthalic ahydride was substituted for the hexahydrophthalic anhydride used in Example 1, to obtain a light-yellow resinous condensation product which was solid at ordinary temperatures. Unlike the decarboxylation condensation product (A), the thus obtained condensation product was soluble in xylene. This condensation product was repeatedly washed with water in a condition of its xylene solution by means of a separating funnel to remove a catalyst DBU, after which the xylene was removed under reduced pressure to obtain 84.3 g of a light-yellow resinous decarboxylation condensation product (B). The evolution of carbon dioxide gas was observed during the reaction.

The decarboxylation condensation product (B) was identified as a compound represented by the formula:

(VIII)

wherein the numerals 1 to 12 show positions of the carbon atoms in the cyclohexane ring and the cyclohexene ring, and the two methyl groups are bonded to the carbon at the 4- or 5-position and to the carbon at the 10- or 11-position, respectively.

From the positions at which the methyl groups are bonded, the decarboxylation condensation product (B) is theoretically considered to be a mixture of four kinds of structural isomers (in which two methyl groups are individually bonded at the 4- and 10-positions, the 4- and 11-positions, the 5- and 10-positions, and the 5- and 11-positions, respectively). However, these structural isomers, of course, have the same rational formula, molecular weight and acid value, and it is substantially impossible to separate the structural isomers in the mixture thereof from one another. Therefore, the decarboxylation condensation product (B) is understood to be a single compound represented by the formula (VIII).

Analysis results for the decarboxylation condensation product (B) are shown below. Elementary analysis results for the obtained decarboxylation condensation product (B) are shown in Table 2.

TABLE 2

| | Condensation product (B) | |
|---|---|---|
| | Analytical value | Theoretical value |
| Carbon (% by weight) | 69.55 | 69.84 |
| Hydrogen (% by weight) | 8.33 | 8.27 |
| Oxygen (% by weight) (balance) | 22.12 | 21.89 |

From these measurement results, the empirical formula was determined to be $C_{17.0}H_{24.3}O_{4.1}$. When these values are compared with the values in $C_{18}H_{24}O_6$, i.e., twice the values in the rational formula $(C_9H_{12}O_3)$ of 4-methylhexahydrophthalic anhydride, it can be seen that said empirical formula clearly lacks 1 mole of $CO_2$.

That is to say, it can be seen that 2 moles of the 4-methylhexahydrophthalic anhydride was converted into the condensation product (B) with release of 1 mole of carbon dioxide gas by the decarboxylation reaction.

Figure 5:
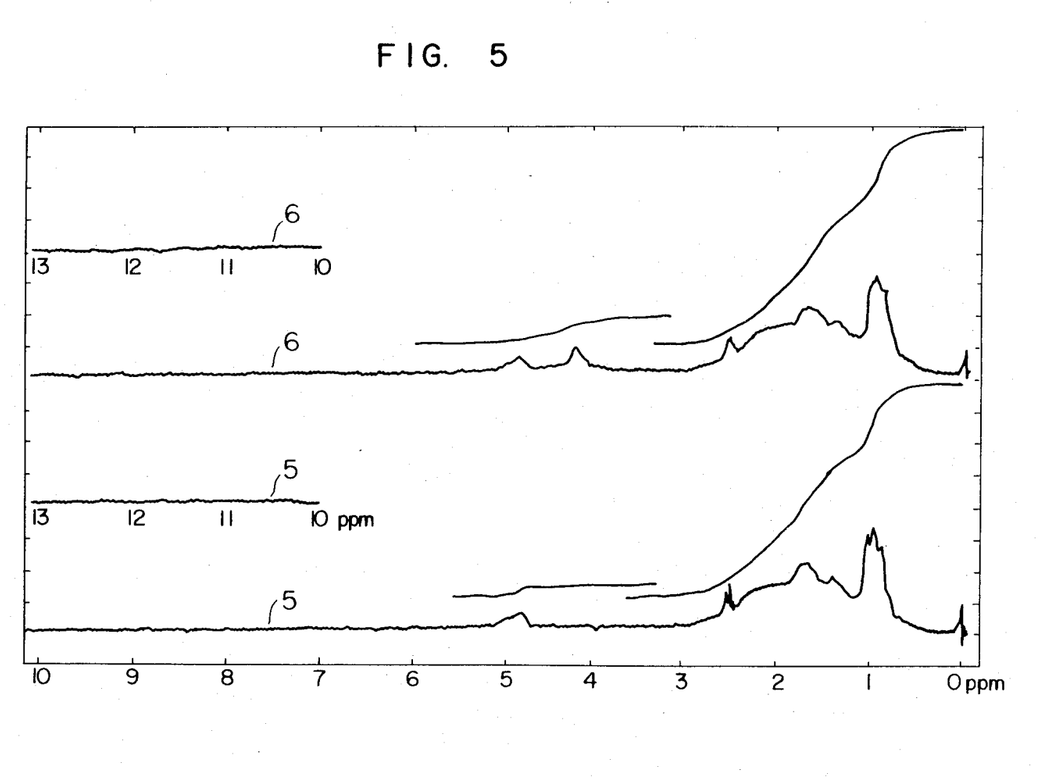
FIG. 5 shows NMR spectra of the decarboxylation condensation product (B) in Example 2.

Next, the results of NMR analysis are shown in FIG. 5. In FIG. 5, the spectrum 5 is that of the decarboxylation condensation product (B) measured in $d_6$-DMSO solvent, and the spectrum 6 is that of the product (B) measured after addition of heavy water to the solvent. In the spectrum 5, the peak due to protons of a carboxyl group is very broad and appears to be absent. This is because the decarboxylation condensation product (B) is a mixture of structural isomers. However, when heavy water was added to the solvent, the spectrum 6 was obtained, and in the spectrum 6, the presence of a carboxyl group is clearly observed. A reason why the peak for protons of methine at the α-position in the lactone ring in the place centering at a δ value of 4.9 ppm does not appears as a single peak but appears as a plurality of overlapped peaks, is that the decarboxylation condensation product (B) is a mixture of structural isomers.

Further, in order to confirm the presence of a carboxyl group and the molecular weight of the decarboxylation condensation product (B), the acid value was measured with potassium hydroxide. As a result, the acid value was found to be 196 (KOH mg/1 g of sample). This value is in good agreement with the theoretical acid value of 192 for a compound with a molecular weight of 292.4 having one carboxyl group.

The above-mentioned analysis results together with the results obtained in Example 1 indicate that the structure of the obtained decarboxylation condensation product (B) is typified by the above formula (VIII).

EXAMPLE 3

A reaction and purification were carried out in the same manner as in Example 2, except that a mixture consisting of 60% by weight of 4-methylhexahydrophthalic anhydride and 40% by weight of 3-methylhexahydrophthalic anhydride was used in place of 4-methylhexahydrophthalic anhydride used in Example 2, to obtain 83.4 g of a light-yellow resinous decarboxylation condensation product (C). The evolution of carbon dioxide gas was observed during the reaction.

The decarboxylation condensation product (C) was identified as a compound represented by the formula:

[IX]

wherein the numerals 1 to 12 show positions of the carbon atoms in the cyclohexane ring and the cyclohexene ring, and the two methyl groups are bonded to the carbon at the 3-, 4-, 5- or 6-position and to the carbon at the 9-, 10-, 11- or 12-position, respectively. From the positions at which the methyl groups are bonded, the decarboxylation condensation product (C) is theoretically considered to be a mixture of 16 kinds of structural isomers. However, all of these structural isomers have the same rational formula, molecular weight and acid value, and it is substantially impossible to separate the structural isomers in the mixtures thereof from one another. Therefore, the decarboxylation condensation product (C) is understood to be a single compound represented by the formula [IX].

Next, analysis results for the decarboxylation condensation product (C) are shown below.

Elementary analysis results for the obtained decarboxylation product (C) are shown in Table 3.

TABLE 3

|  | Condensation product (C) | |
| --- | --- | --- |
|  | Analytical value | Theoretical value |
| Carbon (% by weight) | 69.51 | 69.84 |
| Hydrogen (% by weight) | 8.43 | 8.27 |
| Oxygen (% by weight) (balance) | 22.06 | 21.89 |

From these measurement results, the empirical formula was determined to be $C_{17.0}H_{24.6}O_{4.1}$. When these values are compared with the values in $C_{18}H_{24}O_6$, i.e., twice the values in the rational formula ($C_9H_{12}O_3$) of 4-methylhexahydrophthalic anhydride and 3-methylhexahydrophthalic anhydride, it can be seen that said empirical formula clearly lacks 1 mole of $CO_2$.

That is to say, it can be seen that 2 moles of the mixture of 4-methylhexahydrophthalic anhydride and 3-methylhexahydrophthalic anhydride was converted into the condensation product (C) with release of 1 mole of carbon dioxide gas by the decarboxylation condensation reaction.

Figure 6:
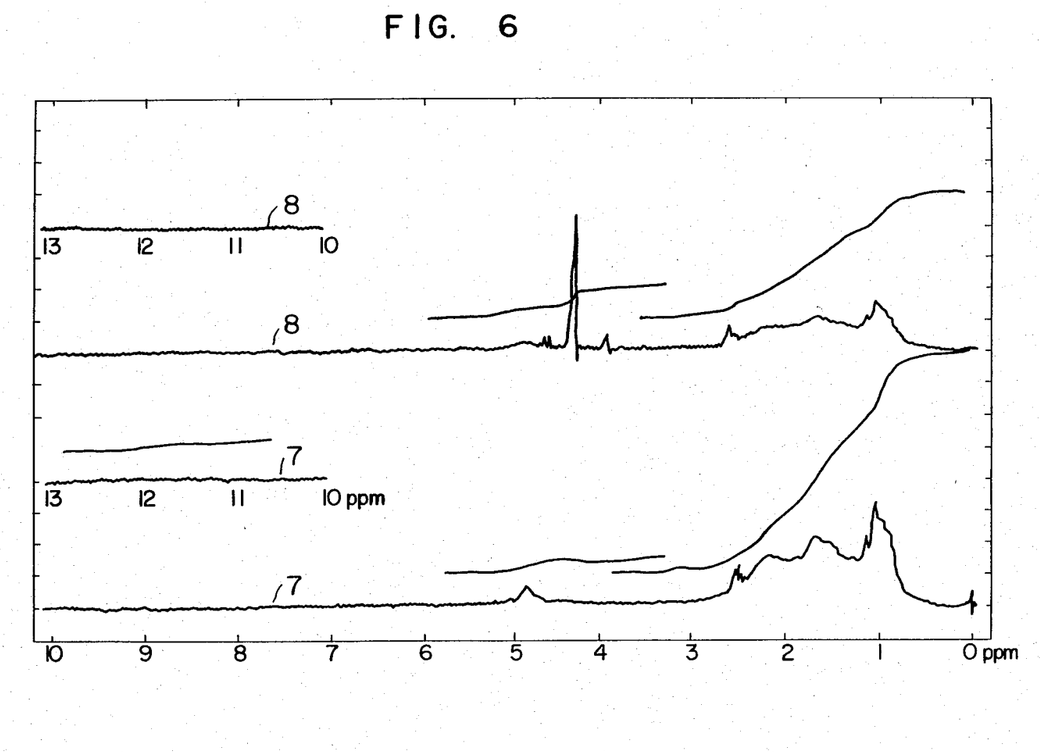
FIG. 6 shows NMR spectra of the decarboxylation condensation product (C) in Example 3.

Next, the results of NMR analysis are shown in FIG. 6. In FIG. 6, the spectrum 7 is that of the decarboxylation condensation product (C) measured in $d_6$-DMSO solvent.

a. No absorption appeared at 12.4 ppm. However, exchange with heavy water resulted in appearance of an absorption at 4.3 ppm, so that the presence of COOH could be confirmed. ———1/24 b. An absorption (somewhat broad) appeared at 4.87 ppm.

The spectrum 8 is that of the condensation product (C) measured after addition of heavy water to the solvent. From these results, the presence of a carboxyl group is revealed as in Example 2.

The IR spectrum showed strong absorptions due to the carboxyl group at 1750 $cm^{-1}$ and 1690 $cm^{-1}$.

Further, in order to confirm the presence of the carboxyl group and the molecular weight of the decarboxylation condensation product (C), the acid value was measured with potassium hydroxide.

As a result, the acid value was found to be 198 (KOH mg/1 g of sample). This value is in good agreement with the theoretical acid value of 192 for a compound with a molecular weight of 292.4 having one carboxyl group.

The above-mentioned analysis results together with the results obtained in Examples 1 and 2 indicate that the obtained decarboxylation condensation product (C) is a compound represented by the above formula [IX].

EXAMPLE 4

In a 18 ⌀ Pirex glass test tube was placed 10 g of hexahydrophthalic anhydride, and 0.1 g of DBU was added, after which the contents of the test tube were heated on an oil bath at 200° C. for 5 hours. The thus obtained product was dissolved in tetrahydrofuran and analyzed by HLC (high-speed liquid chromatography), and the produced amount of a compound represented by the formula (VII) was obtained. The result is shown in Table 4.

EXAMPLES 5 TO 9

A reaction was effected under the same conditions as in Example 4, except that each of the catalysts shown in Table 4 was used in place of that used in Example 4. The analysis results obtained by HLC are shown in Table 4.

COMPARATIVE EXAMPLE 1

A reaction was effected under the same conditions, except that no catalyst was used. The analysis results of HLC are shown in Table 4.

TABLE 4

|  | Catalyst | Yield (%)*1 |
| --- | --- | --- |
| Example 4 | DBU | 100.0 |
| Example 5 | Dibutylaniline | 22.8 |
| Example 6 | 2-Ethyl-4-methylimidazole | 89.7 |
| Example 7 | KOH | 97.1 |
| Example 8 | NaOH | 90.9 |
| Example 9 | NaOCH$_3$ | 85.5 |
| Comparative | No catalyst | 8.2 |

TABLE 4-continued

| | Catalyst | Yield (%)*1 |
|---|---|---|
| Example 1 | | |

*1 $\dfrac{\text{Peak area of bimolecular condensation product}}{\text{Peak area of bimolecular condensation product + peak area of starting material}} \times 100\ (\%)$ In all of Examples 5 to 9, the reaction products contained neither by-product nor unreacted material except each catalyst in addition to a bimolecular condensation product, or contained only the starting hexahydrophthalic anhydride even if they contained any unreacted material.

What is claimed is:

1. A lactone of the formula:

* * * * *